United States Patent
Lee (10) Patent No.: US 9,532,835 B2
(45) Date of Patent: Jan. 3, 2017

(54) METHODS AND SYSTEM FOR IMAGE GUIDED CELL ABLATION WITH MICROSCOPIC RESOLUTION

(71) Applicant: Lumicell, Inc., Wellesley, MA (US)

(72) Inventor: W. David Lee, Brookline, MA (US)

(73) Assignee: Lumicell, Inc., Wellesley, MA (US)

(*) Notice: Subject to any disclaimer, the term of this patent is extended or adjusted under 35 U.S.C. 154(b) by 0 days.

(21) Appl. No.: 14/685,370

(22) Filed: Apr. 13, 2015

(65) Prior Publication Data

US 2015/0216600 A1 Aug. 6, 2015

Related U.S. Application Data

(63) Continuation of application No. 14/219,074, filed on Mar. 19, 2014, now Pat. No. 9,032,965, which is a continuation of application No. 13/314,799, filed on Dec. 8, 2011, now Pat. No. 9,314,304.

(60) Provisional application No. 61/421,077, filed on Dec. 8, 2010.

(51) Int. Cl.
| | |
|---|---|
| A61B 18/24 | (2006.01) |
| A61B 18/20 | (2006.01) |
| A61B 18/02 | (2006.01) |
| A61B 18/14 | (2006.01) |
| A61B 18/00 | (2006.01) |

(52) U.S. Cl.
CPC .............. *A61B 18/24* (2013.01); *A61B 18/20* (2013.01); *A61B 34/20* (2016.02); *A61B 90/39* (2016.02); *A61B 18/02* (2013.01); *A61B 18/14* (2013.01); *A61B 90/30* (2016.02); *A61B 90/361* (2016.02); *A61B 2018/00029* (2013.01); *A61B 2018/00577* (2013.01); *A61B 2018/2085* (2013.01)

(58) Field of Classification Search
CPC . A61B 18/00; A61B 18/18; A61B 2018/1807; A61B 2018/00315; A61B 2018/00571; A61B 2018/00577; A61B 2018/00636; A61B 2018/00642; A61N 5/0613; A61N 5/062; A61N 2005/0626; A61N 2005/0643; A61N 2005/0658
USPC .......... 606/3, 9–12, 16; 607/88–92; 128/898
See application file for complete search history.

(56) References Cited

U.S. PATENT DOCUMENTS

| | | | |
|---|---|---|---|
| 5,268,486 A | 12/1993 | Waggoner et al. | |
| 5,366,860 A | 11/1994 | Bergot et al. | |
| 5,438,989 A | 8/1995 | Hochman et al. | |
| 5,569,587 A | 10/1996 | Waggoner | |
| 5,593,658 A | 1/1997 | Bogdanov et al. | |
| 5,647,368 A | 7/1997 | Zeng et al. | |
| 5,688,221 A | 11/1997 | Yabe et al. | |

(Continued)

FOREIGN PATENT DOCUMENTS

| | | |
|---|---|---|
| EP | 1065250 A1 | 1/2001 |
| EP | 1211294 A1 | 6/2002 |

(Continued)

OTHER PUBLICATIONS

Extended European Search Report for European Application No. 11844820.8 dated Jul. 15, 2014.

(Continued)

*Primary Examiner* — Ahmed Farah
(74) *Attorney, Agent, or Firm* — Wolf, Greenfield & Sacks, P.C.

(57) ABSTRACT

The invention provides systems and method for the removal of diseased cells during surgery.

13 Claims, 1 Drawing Sheet

(56) References Cited

U.S. PATENT DOCUMENTS

| | | | |
|---|---|---|---|
| 5,749,830 A | 5/1998 | Kaneko | |
| 5,769,791 A | 6/1998 | Benaron et al. | |
| 5,800,995 A | 9/1998 | Patonay et al. | |
| 5,954,634 A | 9/1999 | Igarashi | |
| 5,968,479 A | 10/1999 | Ito et al. | |
| 6,027,709 A | 2/2000 | Little et al. | |
| 6,083,486 A | 7/2000 | Weissleder et al. | |
| 6,136,612 A | 10/2000 | Della Ciana et al. | |
| 6,180,086 B1 | 1/2001 | Achilefu et al. | |
| 6,256,530 B1 | 7/2001 | Wolfe | |
| 6,485,413 B1 | 11/2002 | Boppart et al. | |
| 6,537,211 B1 | 3/2003 | Wang et al. | |
| 6,592,847 B1 | 7/2003 | Weissleder et al. | |
| 6,620,621 B1 | 9/2003 | Cohenford et al. | |
| 6,631,230 B1 | 10/2003 | Campbell | |
| 6,667,159 B1 | 12/2003 | Walt et al. | |
| 6,737,247 B2 | 5/2004 | Bogdanov et al. | |
| 6,834,238 B1 | 12/2004 | Hochman | |
| 7,128,894 B1 | 10/2006 | Tannous et al. | |
| 7,285,089 B2 | 10/2007 | Viellerobe et al. | |
| 7,344,530 B2 * | 3/2008 | Bischof | A61B 18/02 128/898 |
| 7,383,076 B2 | 6/2008 | Ntziachristos et al. | |
| 7,383,077 B2 | 6/2008 | Zeng | |
| 7,452,727 B2 | 11/2008 | Hennig et al. | |
| 7,498,029 B2 | 3/2009 | Hasan et al. | |
| 8,815,214 B2 | 8/2014 | Rajopadhye et al. | |
| 8,983,581 B2 * | 3/2015 | Bawendi | A61B 5/0071 382/128 |
| 9,032,965 B2 * | 5/2015 | Lee | A61B 18/20 128/898 |
| 9,155,471 B2 * | 10/2015 | Lee | A61B 5/0071 |
| 2002/0064794 A1 | 5/2002 | Leung et al. | |
| 2002/0115862 A1 | 8/2002 | Czerney et al. | |
| 2002/0165456 A1 | 11/2002 | Canpolat et al. | |
| 2003/0039741 A1 | 2/2003 | Carver et al. | |
| 2003/0044353 A1 | 3/2003 | Weissleder et al. | |
| 2003/0138378 A1 | 7/2003 | Hashimshony | |
| 2004/0015062 A1 | 1/2004 | Ntziachristos et al. | |
| 2004/0071332 A1 | 4/2004 | Bruce et al. | |
| 2004/0253593 A1 | 12/2004 | Cai et al. | |
| 2005/0130167 A1 | 6/2005 | Bao et al. | |
| 2005/0171434 A1 | 8/2005 | Madden et al. | |
| 2005/0207668 A1 | 9/2005 | Perchant et al. | |
| 2005/0214221 A1 | 9/2005 | Poss et al. | |
| 2006/0009590 A1 | 1/2006 | Kozlowski et al. | |
| 2006/0165350 A1 | 7/2006 | Gelikonov et al. | |
| 2006/0188797 A1 | 8/2006 | Roy et al. | |
| 2006/0253107 A1 | 11/2006 | Hashimshony et al. | |
| 2007/0036725 A1 | 2/2007 | Bogyo et al. | |
| 2007/0160279 A1 | 7/2007 | Demos | |
| 2007/0179174 A1 | 8/2007 | Bachurin et al. | |
| 2007/0182959 A1 | 8/2007 | Maier et al. | |
| 2007/0255169 A1 | 11/2007 | Hashimshony et al. | |
| 2007/0260156 A1 | 11/2007 | Hashimshony | |
| 2008/0015446 A1 | 1/2008 | Mahmood et al. | |
| 2008/0029711 A1 | 2/2008 | Viellerobe et al. | |
| 2008/0039742 A1 | 2/2008 | Hashimshony et al. | |
| 2008/0076674 A1 | 3/2008 | Litman et al. | |
| 2008/0103373 A1 | 5/2008 | Matter et al. | |
| 2008/0154102 A1 | 6/2008 | Frangioni et al. | |
| 2008/0193373 A1 | 8/2008 | Stritzker et al. | |
| 2008/0193431 A1 | 8/2008 | Zheng et al. | |
| 2008/0260646 A1 | 10/2008 | Keller et al. | |
| 2008/0287750 A1 | 11/2008 | Hashimshony et al. | |
| 2009/0004116 A1 | 1/2009 | Bhaumik et al. | |
| 2009/0028788 A1 | 1/2009 | Achilefu | |
| 2009/0123381 A1 | 5/2009 | Hsieh et al. | |
| 2009/0299196 A1 | 12/2009 | Bawendi et al. | |
| 2010/0189658 A1 | 7/2010 | Wendt et al. | |
| 2010/0262017 A1 | 10/2010 | Frangioni et al. | |
| 2010/0286044 A1 | 11/2010 | Litman et al. | |
| 2010/0298554 A1 | 11/2010 | Laikhter et al. | |
| 2010/0321772 A1 | 12/2010 | Reimer et al. | |
| 2011/0009694 A1 | 1/2011 | Schultz et al. | |
| 2011/0021908 A1 | 1/2011 | Lee et al. | |
| 2011/0028790 A1 | 2/2011 | Farr et al. | |
| 2011/0104071 A1 | 5/2011 | Lee et al. | |
| 2011/0159566 A1 | 6/2011 | Josephson et al. | |
| 2012/0150164 A1 | 6/2012 | Lee et al. | |
| 2014/0088384 A1 * | 3/2014 | Basilion | A61B 5/0071 600/317 |
| 2014/0207126 A1 | 7/2014 | Bianchi | |
| 2014/0207129 A1 | 7/2014 | Lee et al. | |
| 2014/0243934 A1 | 8/2014 | Vo-Dinh et al. | |
| 2014/0276102 A1 | 9/2014 | Lee et al. | |
| 2014/0276103 A1 | 9/2014 | Lee et al. | |
| 2014/0301950 A1 | 10/2014 | Lee et al. | |
| 2015/0216416 A1 * | 8/2015 | Bawendi | A61B 5/0071 600/431 |

FOREIGN PATENT DOCUMENTS

| | | |
|---|---|---|
| EP | 1223197 A2 | 7/2002 |
| EP | 1273584 A1 | 1/2003 |
| WO | WO 97/13810 A1 | 4/1997 |
| WO | WO 98/47538 A2 | 10/1998 |
| WO | WO 00/53678 A1 | 9/2000 |
| WO | WO 01/90253 A1 | 11/2001 |
| WO | WO 02/24815 A1 | 3/2002 |
| WO | WO 02/056670 A2 | 7/2002 |
| WO | WO 03/105814 A1 | 12/2003 |
| WO | WO 2008/088865 A2 | 7/2008 |

OTHER PUBLICATIONS

International Preliminary Report on Patentability for PCT/US2010/036433 mailed Dec. 8, 2011.

International Preliminary Report on Patentability for PCT/US2011/062527 mailed Jun. 13, 2013.

International Preliminary Report on Patentability for PCT/US2014/027287 mailed Sep. 24, 2015.

International Preliminary Report on Patentability for PCT/US2014/027769 mailed Sep. 24, 2015.

International Search Report and Written Opinion for PCT/US2010/036433 mailed Sep. 6, 2010.

International Search Report and Written Opinion for PCT/US2011/062527 mailed Jun. 15, 2012.

International Search Report and Written Opinion for PCT/US2014/027287 mailed Jul. 18, 2014.

International Search Report and Written Opinion for PCT/US2014/027769 mailed Oct. 30, 2014.

[No Author Listed], Cathepsin Activatable Fluorescent Probe. Clinical Trials. Jun. 21, 2012. (https://clinicaltrials.gov/archive/NCT01626066/2012_06_21) [last accessed May 27, 2015].

Invitation to Pay Additional Fees for PCT/US2014/027769 mailed Aug. 14, 2014.

Anikijenko et al., In vivo detection of small subsurface melanomas in athymic mice using noninvasive fiber optic confocal imaging. J Invest Dermatol. Dec. 2001;117(6):1442-8.

Bates et al., Short-range spectroscopic ruler based on a single-molecule optical switch. Phys Rev Lett. Mar. 18, 2005;94(10):108101. Epub Mar. 15, 2005.

Bigio et al., Diagnosis of breast cancer using elastic-scattering spectroscopy: preliminary clinical results. J Biomed Opt. Apr. 2000;5(2):221-8.

Blum et al., Noninvasive optical imaging of cysteine protease activity using fluorescently quenched activity-based probes. Nat Chem Biol. Oct. 2007;3(10):668-77. Epub Sep. 9, 2007.

Bogdanov, Jr. et al., Long-circulating blood pool imaging agents. Adv Drug Del Rev. 1995;16:335-48.

Brigman, Preliminary Analysis of Phase 1, First-In-Human, Cathepsin Activated Tumor Imaging Probe. Presentation. Nov. 2013 29 pages.

Cheng et al., Near-infrared fluorescent RGD peptides for optical imaging of integrin alphavbeta3 expression in living mice. Bioconjug Chem. Nov.-Dec. 2005;16(6):1433-41.

Cuneo et al., Imaging primary mouse sarcomas after radiation therapy using cathepsin-activatable fluorescent imaging agents. Int (56) References Cited

OTHER PUBLICATIONS

J Radiat Oncol Biol Phys. May 1, 2013;86(1):136-42. doi: 10.1016/j.ijrobp.2012.12.007. Epub Feb. 4, 2013.
De Grand et al., Tissue-like phantoms for near-infrared fluorescence imaging system assessment and the training of surgeons. J Biomed Opt. Jan.-Feb. 2006;11(1):014007.
Demos et al., Near-infrared autofluorescence imaging for detection of cancer. J Biomed Opt. May-Jun. 2004;9(3):587-92.
Freireich et al., Quantitative comparison of toxicity of anticancer agents in mouse, rat, hamster, dog, monkey, and man. Cancer Chemother Rep. May 1966;50(4):219-44.
Funovics et al., Protease sensors for bioimaging. Anal Bioanal Chem. Nov. 2003;377(6):956-63. Epub Sep. 3, 2003.
Geigy Pharmaceuticals, Body Surface Area of Adults. In: Scientific Tables. Diem and Lentner, Ed., Ciba-Geigy Ltd. Ardsley, New York. 1970:537.
Goldberg et al., Radiofrequency tissue ablation: importance of local temperature along the electrode tip exposure in determining lesion shape and size. Acad Radiol. Mar. 1996;3(3):212-8.
Graves et al., A submillimeter resolution fluorescence molecular imaging system for small animal imaging. Med Phys. May 2003;30(5):901-11.
Gray et al., Dual-mode laparoscopic fluorescence image-guided surgery using a single camera. Biomed Opt Express. Aug. 1, 2012;3(8):1880-90. doi: 10.1364/BOE.3.001880. Epub Jul. 17, 2012.
Hart et al., Cell binding and internalization by filamentous phage displaying a cyclic Arg-Gly-Asp-containing peptide. J Biol Chem. Apr. 29, 1994;269(17):12468-74.
Holland et al., Chapter 4. Biodegradable polymers. In: Advances in Pharmaceutical Sciences. Ganderton et al., eds. vol. 6. 1992:101-164.
Holsinger et al., Use of the photonic band gap fiber assembly CO2 laser system in head and neck surgical oncology. Laryngoscope. Jul. 2006;116(7):1288-90.
Hsiung et al., Detection of colonic dysplasia in vivo using a targeted heptapeptide and confocal microendoscopy. Nat Med. Apr. 2008;14(4):454-8. doi: 10.1038/nm1692. Epub Mar. 16, 2008.
Kong et al., Comparative analysis of different laser systems to study cellular responses to DNA damage in mammalian cells. Nucleic Acids Res. May 2009;37(9):e68. doi: 10.1093/nar/gkp221. Epub Apr. 7, 2009.
Licha et al., Synthesis and characterization of cyanine dyes as contrast agents for near-infrared imaging. SPIE. 1996;2927:192-8.
Lin et al., Novel near-infrared cyanine fluorochromes: synthesis, properties, and bioconjugation. Bioconjug Chem. May-Jun. 2002;13(3):605-10.
Liu et al., Hands-free, wireless goggles for near-infrared fluorescence and real-time image-guided surgery. Surgery. May 2011;149(5):689-98. doi: 10.1016/j.surg.2011.02.007.
Mahmood et al., Near-infrared optical imaging of protease activity for tumor detection. Radiology. Dec. 1999;213(3):866-70.
Moats et al., A "Smart" Magnetic Resonance Imaging Agent That Reports on Specific Enzymatic Activity. Angew Chem Int Ed Engl. 1997;36(7):726-8.
Mullenix et al., Secondary operations are frequently required to complete the surgical phase of therapy in the era of breast conservation and sentinel lymph node biopsy. Am J Surg. May 2004;187(5):643-6.
Negrin et al., In vivo-in vitro study of biodegradable methadone delivery systems. Biomaterials. Mar. 2001;22(6):563-70.
Palen et al., Substrate specificity of a hypothalamic neurosecretory granule enzyme capable of processing pro-gonadotropin releasing hormone precursor protein. Peptides. Jan.-Feb. 1987;8(1):21-4. Abstract only.
Poul et al., Selection of tumor-specific internalizing human antibodies from phage libraries. J Mol Biol. Sep. 1, 2000;301(5):1149-61.
Railton et al., Myocardial scintigraphy with I-123 heptadecanoic acid as a test for coronary heart disease. Eur J Nucl Med. 1987;13(2):63-6.
Ramanujam et al., Fast and noninvasive fluorescence imaging of biological tissues in vivo using a flying-spot scanner. IEEE Trans Biomed Eng. Sep. 2001;48(9):1034-41.
Reinisch, Laser physics and tissue interactions. Otolaryngol Clin North Am. Dec. 1996;29(6):893-914.
Rogakou et al., Megabase chromatin domains involved in DNA double-strand breaks in vivo. J Cell Biol. Sep. 6, 1999;146(5):905-16.
Singletary et al., Revision of the American Joint Committee on Cancer staging system for breast cancer. J Clin Oncol. Sep. 1, 2002;20(17):3628-36.
Tung et al., In vivo imaging of proteolytic enzyme activity using a novel molecular reporter. Cancer Res. Sep. 1, 2000;60(17):4953-8.
Tyagi et al., Multicolor molecular beacons for allele discrimination. Nat Biotechnol. Jan. 1998;16(1):49-53.
Vaidya et al., Intraoperative T staging in radical retropubic prostatectomy: is it reliable? Urology. May 2001;57(5):949-54.
Van Eenige et al., Clinical value of studies with radioiodinated heptadecanoic acid in patients with coronary artery disease. Eur Heart J. Mar. 1990;11(3):258-68.
Vogel et al., Mechanisms of pulsed laser ablation of biological tissues. Chem Rev. Feb. 2003;103(2):577-644.
Weissleder et al., In vivo imaging of tumors with protease-activated near-infrared fluorescent probes. Nat Biotechnol. Apr. 1999;17(4):375-8.
Weissleder et al., In vivo magnetic resonance imaging of transgene expression. Nat Med. Mar. 2000;6(3):351-4.
Yang et al., Presentation, 2010 IVIS Imaging System from Caliper LifeSciences, 104 slide presentation 52 pages.
Zaheer et al., In vivo near-infrared fluorescence imaging of osteoblastic activity. Nat Biotechnol. Dec. 2001;19(12):1148-54.
Zornig et al., Re-excision of soft tissue sarcoma after inadequate initial operation. Br J Surg. Feb. 1995;82(2):278-9.

\* cited by examiner

METHODS AND SYSTEM FOR IMAGE GUIDED CELL ABLATION WITH MICROSCOPIC RESOLUTION

RELATED APPLICATIONS

This Application is a continuation and claims the benefit under 35 U.S.C. §120 of U.S. application Ser. No. 14/219,074, entitled "METHODS AND SYSTEM FOR IMAGE GUIDED CELL ABLATION WITH MICROSCOPIC RESOLUTION" filed on Mar. 19, 2014, which is herein incorporated by reference in its entirety. Application Ser. No. 14/219,074 is a continuation and claims the benefit under 35 U.S.C. §120 of U.S. application Ser. No. 13/314,799, entitled "METHODS AND SYSTEM FOR IMAGE GUIDED CELL ABLATION WITH MICROSCOPIC RESOLUTION" filed on Dec. 8, 2011, which is herein incorporated by reference in its entirety. Application Ser. No. 13/314,799 claims priority under 35 U.S.C. §119(e) to U.S. Provisional Application Ser. No. 61/421,077, entitled "METHODS AND SYSTEMS FOR IMAGE GUIDED CELL ABLATION WITH MICROSCOPIC RESOLUTION" filed on Dec. 8, 2010, which is herein incorporated by reference in its entirety.

FIELD OF INVENTION

The present invention relates generally to the ablation of abnormal cells guided by imaging of such cells during surgical procedures.

BACKGROUND OF INVENTION

A major challenge of oncology surgery is removing cancer cells from the tumor bed with certainty. Residual cancer, which refers to cancer cells left behind after the initial resection surgery, can lead to local recurrence, increased rates of metastasis, and poorer outcomes. Currently, there is a high rate of secondary surgeries because cancer cells are found at the margins of the resected mass during post-operative pathological analysis of the tumor. For example, 50% of breast conserving lumpectomies (Mullenix et al., Am. J. Surg., 187:643-646, 2004), 35% of limb-sparing sarcoma surgeries (Zornig et al., Br. J. Surg., 82:278-279, 1995), and 37% or radical prostatectomies (Vaidya et al., Urology, 57:949-954, 2001) fail to completely remove cancer cells during the initial surgery. One of the leading causes of not being able to remove all the cancer cells in the tumor bed is the lack of an intraoperative visualization technology that can guide the surgeon to identify and remove the diseased cell. In many cases, effective and total resection of cancers in organs is further complicated because essential adjacent structures need to be spared (for example brain surgeries or other surgeries where important nerves or blood vessels are nearby).

Standard assessment of a resection is performed by inking the outside of the excised tissue, freezing it and then examining the edge of specimen sections by light microscopy (known as frozen section analysis). The presence of tumor cells at the inked margin, which is referred to as a positive margin, indicates that tumor cells remain behind in the tumor bed. Although margin assessment of a frozen section can take place during surgery, time constraints normally limit this assessment to small areas of the tumor. Therefore, this approach is prone to sampling error. The remaining excised tissue is fixed in formalin and it may take several days before the pathologist can complete the analysis to identify a positive margin. If a positive margin is identified, patients most often require a repeat surgical resection, leading to increased patient morbidity and higher healthcare costs. Other intraoperative cancer detection technologies have been developed including radio-frequency (RF) spectroscopy analysis of the surface of resected tumors (Allweis et al., Am. J. Surg., 187:643-646, 2004), Raman and elastic scattering spectroscopy (Bigio et al., J. Biomed. Opt. 5:221-228, 2000) and tissue autofluorescence (Demos et al., J. Biomed. Opt., 9:587-592, 2004). However, each of these technologies lacks the resolution, sensitivity and ease of use required for rapid assessment of microscopic residual cancer within the entire tumor and does not provide means of tissue removal.

A common method used to destroy cells in situ is laser ablation therapy. Laser ablation therapy refers to the destruction of tissue by delivering heat in the form of light into a small volume. Typically, the laser light is presented in short pulses to reduce damage and overheating of surrounding healthy tissue. The amount of tissue being ablated is controlled by the size of the laser focal spot (0.2-3 mm in diameter), intensity and duration of exposure. At the focal spot, temperatures will reach 100.degree. C. which causes vaporization of the tissue due to evaporation of interstitial water (Gough-Palmer et al., Laryngoscope, 116:1288-1290, 2006). At about 1.5 diameters, temperatures reaching 50.degree. C.-54.degree. C. will induce instant cell death, rapid coagulative necrosis, and immediately cauterize the wound limiting the blood loss to a minimum (Goldberg et al., Acad. Radiol., 3:212-218, 1996).

To reach the desired depth of ablation, the wavelength of the laser light has to be carefully chosen. For example, a potassium titanyl phosphate laser (KTP) producing light at a 532 nm wavelength is typically used for ablation of tissue limited to surface treatment (for example, skin cancer and tumors at the periphery of organs), as its depth of penetration is only 900 .mu.m. Carbon dioxide lasers are also used for surface ablation as its 10.6 .mu.m wavelength is heavily absorbed by water inside tissue limiting its penetration depth to approximately 300 .mu.m. For ablation of diseased tissue below the surface, Nd:YAG lasers, operating at a wavelength of 1064 nm, provide penetration depths up to 15 mm (Reinisch, Otoralyngol. Clin. North. Am., 29:893-914, 1996).

Laser ablation procedures are usually non- or minimally-invasive and guided by standard imaging techniques. Currently, laser ablation has been used intraoperatively to remove visible cancer nodes in lung tumors, unresectable liver metastasis, small breast cancers and laryngeal cancers. However, ablation therapy lacks cellular resolution because it is often limited by the spatial resolution provided by the guiding imaging techniques; thus, it can easily leave millions of cancer cells behind. For example, the Gamma Knife unit used in brain surgery has a theoretical accuracy of 0.2 mm but it is limited by the imaging resolution of 2 mm and positioning and excision accuracy of the surgeon.

Thus, a need exists for an intraoperative and real-time cancer cell detection and therapy device at a single-cell level to ensure thorough examination of the tumor bed for residual cancer while providing guidance for additional tissue removal. A single-cell image detection technology could be use to guide an automatic cell ablation system to destroy the cancer cells as soon as they are detected. The combined system will give the surgeon the ability to remove cancer cells at an unprecedented single cell level while providing a minimum impact on the healthy tissue. This will address the difficulty of removing residual cancer in complicated open and endoscopic surgeries such as brain, sarcoma, and colon.

SUMMARY OF INVENTION

The invention is based on a system which is capable of detecting abnormal cells at a single cell resolution and treating the abnormal cells with laser ablative therapy. The laser and imaging system are preferentially detecting and treating surface cells. Although abnormal cells that are cancerous in nature are ideally targeted, the system and methods can be adapted to other abnormal cells or tumor-associated cells as well. Alternatively, other energy sources can be used in place of the laser, for example radiofrequency ablation or cryoablation.

Furthermore, the invention also includes methods for intraoperative in-vivo imaging and treatment using said device. Subjects can be either human or animal. Preferably, the subject is given a fluorescent, activatable probe, administered orally, systemically, via bolus injection, via surface application or other established method. Alternatively an antibody probe can be used or the endogenous fluorescent difference between cancer cells and healthy cells may be used without an imaging agent or probe. The probe then is allowed to reach the target tissue and is activated by the tissue at the target location. During the surgical operation, the diseased tissue is exposed by the surgeon and the bulk diseased tissue is removed, if possible. The imaging device is then used to identify and treat the residual abnormal cells.

In one aspect the invention provides an in vivo method of treating abnormal cells by administering a composition comprising a molecular imaging probe to a tissue of a subject and obtaining an in situ image of the tissue where the image allows for the detection of one or more diseased cells, if present in the tissue and treating the diseased cell. The subject is a mammal such as a human.

The composition is administered systemically to the subject or applied to the surface of the tissue, such as by spraying or painting. Alternatively the composition is administered on a film or sponge.

In some embodiments the cells are treated with light energy, such as a laser. Cells are ablated by a laser by locating one or more diseased cells in situ using an imaging system, transferring the location of the diseased cell to a laser guiding system to move the laser over the target cell for ablation, imaging the actual location of the laser using the imaging system to provide spatial feedback to the laser guiding system, adjusting the location of the laser if necessary based on the aforementioned feedback and ablating detected diseased cell(s). Optionally, the method includes an additional feedback algorithm after the ablation of diseased cells to post-image the treatment tissue and verify that the diseased cells have been correctly treated. The imaging system is a single-cell resolution imaging system. The laser guiding system consists of one or more galvanometer mirrors, MEMS mirrors, acousto-optic deflectors, micromirrors, acousto-optic modulators used as deflectors, piezo-electrial mirrors, electro-optical deflectors, polygonal mirrors, or planar mirrors on a rotating shaft.

The molecular probe can be any molecule that gives us a contrast between the diseased cells and normal tissue and can include either activated, ligand or clearance differential. The activated can be activated by enzymes and can be a flourochrome plus a quencher or two flourochromes in a self-quenching configuration. A ligand based probe would be for instance a flourochrome together with a targeting antibody. A clearance differential probe would be a molecule with a fluorescent label and a pharmacokinetic modifier that clears the probe preferentially from the healthy tissue leaving the cancer cells and/or tumor associated inflammation cells labeled.

The molecular imaging probe is activated by enzymes. In another aspect the imaging probe contain one or more fluorochromes and one or more dark quenchers. Exemplary fluorochromes include Cy3, Cy3.5, Cy5, Alexa 568, Alexa 546, Alexa 610, Alexa 647, ROX, TAMRA, Bodipy 576, Bodipy 581, Bodipy TR, Bodipy 630, VivoTag 645, and Texas Red.

Exemplary dark quenchers include a QSY quencher, a dabcyl quencher, an Iowa Black quencher, and a Black Hole quencher. The QSY quencher is QSY21, QSY7, QSY9, or QSY35. The Iowa Black quencher is Iowa Black FQ or Iowa black RQ. In some aspects the imaging probe is in the visible light spectrum of 350-670 nm. Optionally, imaging probe includes a pharmacokinetic modifier. The probe is optimally imaged at less than 2 hours after administration. Alternatively, the probe is optimally imaged at between 12 and 36 hours after administration.

In some aspects the molecular imaging probe contains a targeting moiety and an imaging moiety. A targeting moiety binds specifically to CD20, CD33, carcinoembryonic antigen (CEA), alpha fetoprotein (AFP), CA125, CA19-9, prostate specific antigen (PSA), human chorionic gonadotropin (HCG), acid phosphatase, neuron specific enolase, galacatosyl transferase II, immunoglobulin, CD326, her2NEU, EGFR, PSMA, TTF1, Muc, immature glycoslytaion, an EMT marker, a cathepsin, or an enzyme. The imaging moiety is a fluorochrome such as Cy3, Cy3.5, Cy5, Alexa 568, Alexa 546, Alexa 610, Alexa 647, ROX, TAMRA, Bodipy 576, Bodipy 581, Bodipy TR, Bodipy 630, VivoTag 645, and Texas Red.

The diseased cell is within 1 cm from the surface. The diseased cell is for example a cancer cell, a central nervous cell, a cardiac cell, a bone cell, a tendon cell, or a muscle cell.

Also included in the invention is a medical imaging and treatment system containing:

(a) an excitation source configured to cause an object having a plurality of cells to emit and fluoresce light;

(b) an optical receptor configured to receive the light from the object;

(c) an image processor;

(d) an energy source sufficient for destroying one or more cells; and (e) a feedback system configured to detect the condition of each cell and apply treatment to detected diseased cells.

The image processor contains a field of view (FOV) substantially greater than a diameter of a cell of the object and an analysis resolution substantially matched to the diameter of a cell of the object and configured to receive and analyze the light corresponding to each cell in the FOV.

The cells are treated using light energy. In some aspects the light energy is delivered by a plurality of lights. For example, an optical fiber bundle collects and distributes light to the cells.

In another embodiment the cells are treated using laser ablation, radio frequency ablation or cryo-ablation. The laser is controlled by a laser guiding system comprising of one or more galvanometer mirrors, MEMS mirrors, acousto-optic deflectors, micromirrors, acousto-optical modulators used as deflectors, piezo-electrial mirrors, electro-optical deflectors, polygonal mirrors, or planar mirrors on a rotating shaft.

A single light source may be used for both the fluorescent excitation and then a higher power setting would provide the ablation function.

The light energy is between 100 nm and 2500 nm. In some aspects the light energy is pulsed. For example, the pulse is for duration less than 100 ns. In some aspects, the light energy imparts delayed cell death.

The feedback system consists of:

(a) locating the diseased cell in situ using an imaging system;

(b) transferring the location of the diseased cell to a laser guiding system to move the laser over the target cell for ablation (c) imaging the actual location of the laser using the imaging system to provide spatial feedback to the laser guiding system (d) adjusting the location of the laser if necessary based on the aforementioned feedback (e) ablating detected diseased cell(s).

Optionally the system further contains an additional feedback algorithm after the ablation of diseased cells to post-image the treatment tissue and verify that the diseased cells have been correctly treated. In some embodiments the system contains a fluid reservoir which flushes cell area with fluid to remove debris created during ablative process. Additionally, in some embodiments the system contains a fluid reservoir which flushes cell area with fluid to cool tissue as ablative heat destroys abnormal cells, preventing excess treatment to healthy tissue.

In another embodiment, the method does not require an imaging probe. Instead, an imaging method (e.g. fluorescence, spectroscopy, or other imaging technique) is used to determine which cells to ablate.

In another embodiment, the system requires a light source to image the tissue. In some aspects, the system does not excite an imaging agent.

As used herein, "probe" means an identifiable molecule which is used to detect the presences of other molecules.

As used herein, "fluorochrome" means a molecule which becomes fluorescent by absorbing energy (light) at one or more specific wavelengths by exciting ground-state electrons into a higher energy level and then emitting energy (light) at one or more slightly different wavelengths when the excited electrons return to the ground-state energy level.

As used herein, "dark quencher" means a molecule which absorbs light radiation at one or more specific wavelengths and dissipates the energy absorbed in the form of heat; thus, a dark quencher does not emit fluorescent light.

As used herein, "pharmacokinetic modifier" means a molecule which is attached to the molecular imaging probe which inhibits undesired biodegradation, clearance, or immunogenicity of the probe.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

DETAILED DESCRIPTION OF INVENTION

The present invention relates to the design of a system which is able to simultaneously detect abnormal cells and treat the cells with a laser ablation. The invention applies to the removal of diseased cells in surgery. Cancerous tissue removal is one such application though not the only one as abnormal cells in various central nervous system disorders (e.g. Parkinson's disease) or various cardiovascular system disorders (e.g. ischemia), or various orthopedic disorders (e.g. osteoporosis) could be a target for removal.

Figure 1:
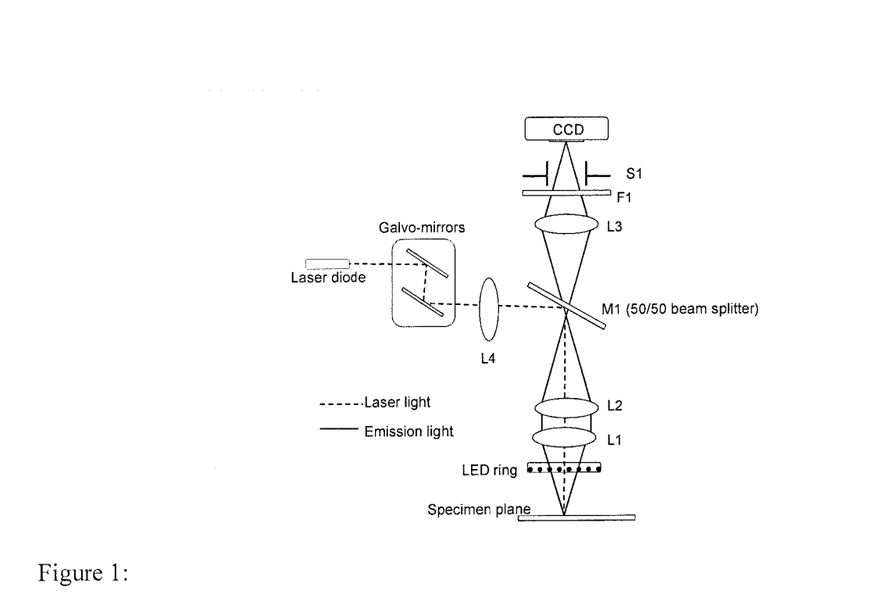
FIG. 1: Optical layout of laser and imaging system. Fluorescence excitation is provided by a ring of LED. Lenses L1 and L2 collect the image of the specimen plane and relay it to lens L3, which focuses it onto the CCD camera. Band-pass filter F1 blocks all wavelengths except the fluorescence emission of the target. A laser diode provides high intensity illumination to induce photobleaching of the target to simulate ablation. The laser light is actively directed by a 2-dimensional set of galvo-mirrors. Lens L4 adjusts the focus of the laser beam at the specimen plane. The laser light is brought into the optical axis by reflecting off a 50-50 beam splitter (M1). During exposure of high laser intensity, shutter S1 prevents light from damaging and/or saturating the CCD.

FIG. 1 shows a schematic of one example of such a system. The imaging system consists of a number of components including an excitation source such that one or more diseased cells are caused to emit fluorescent light, an optical receptor to receive the emitted light from the diseased cells, an image processor, an energy source for destroying detected diseased cells, and a feedback system for detecting the condition of each cell and applying treatment to the detected diseased cells.

In the image detection portion of the system of FIG. 1, fluorescence excitation is provided by a ring of LED. The target abnormal specimen contains an activated fluorescent probe such that the probe is excited by one wavelength of light and emits a second, distinct wavelength. Lenses L1 and L2 collect the image of the specimen plane and relay it to lens L3, which focuses it onto the charge-coupled device (CCD) camera (or alternatively an avalanche photodiode: APD array or complementary metal-oxide semiconductor: CMOS). Band-pass filter F1 blocks all wavelengths including the excitation fluorescence of the LED ring and allows the fluorescence emission of the target to reach the camera.

The image detection portion of the system provides a wide field of view (FOV) with an analysis resolution substantially matched to the size of a cell by matching a given cell with one or more pixels of a CCD, APD, or CMOS array such that the FOV of any pixel is one cell or less. This provides a desirable photon flux rate (photons/sec-area) and desirably controls the background emission (auto fluorescence) which, along with the dark count, determines the signal-to-noise ratio of the instrument and its sensitivity. If the field of view of a pixel contains several cells and only one is a cancer cell that has illuminated molecular probes, the average photon flux rate to the pixel will be reduced and the ratio of the signal-to-background noise will be, likewise, reduced. Furthermore, if multiple cancers cells are closely spaced, the device will still be able to differentiate individual cells.

For the laser ablation portion of the system of FIG. 1, the laser light is actively directed by a 2-dimensional set of galvo-mirrors. Lens L4 adjusts the focus of the laser beam at the specimen plane. The laser light is brought into the optical axis by reflecting off a 50-50 beam splitter (M1). During exposure of high laser intensity, shutter 51 prevents light from damaging and/or saturating the CCD.

The pair of galvo-mirrors will provide 2-dimensional control of the location of the laser in the specimen plane. Galvanometer-mirrors (or galvo-mirrors) consist of a galvanometer-based scanning motor with a mirror mounted on the motor shaft and a detector that provides feedback on the current angular position to the controller. Galvo-mirrors have a precision in the range of 15 .mu.radians, a step response time of 300 .mu.s and a small angle bandwidth of 1 kHz, thus providing fast control of the laser. These mirrors are usually employed commercially for fast laser engraving and bar code reading. Galvo-mirrors are also used in research for laser scanning applications such as optical tweezers and some types of confocal microscopy set ups.

The path length between the galvo-mirrors and the laser focusing lens (L4) can be adjusted in order to achieve full coverage of the camera field of view at the largest angular deflection (laser location is proportional to the path length multiplied by tangent of the angular deflection of galvo-mirrors). The laser will be brought into the optical imaging path via a 50-50 beam splitter to reflect 50% of the light on the specimen plane. In contrast to a dichroic mirror, this 50-50 beam splitter also allows some of the laser light in the specimen plane to reach the camera, which can be used for the imaging and a feedback algorithm. The distance between lenses L4 and L2 can be set such that a 100 .mu.m laser spot diameter (or any other desired spot diameter) can be obtained at the specimen plane—this distance can be mathematically determined once all the parameters involved (input beam diameter and focal lengths of all the lenses) are determined.

A calibration curve to correlate the beam angular deflection by the galvo-mirrors with the x-y location of the laser beam in pixel coordinates can be empirically determined. The galvo-mirrors can be scanned over a range of angles while an image is acquired at each angular step to determine the pixel location of the beam spot. To avoid damage to the camera chip and signal saturation, the laser intensity can be set at a reduced power during this calibration. Also, the fluorescence emission filter (F1) can be removed to avoid filtering out the laser light before reaching the camera. The calibration curve can be fitted to a suitable polynomial function in the form of (.alpha., .beta.)=f(xp, yp), where .alpha. and .beta. correspond to the angular deflection of each galvo-mirror, respectively, and xp and yp correspond the x- and y-coordinates in camera pixels.

Once the laser calibration curve is known, a detected abnormal cell can be treated. The camera pixel locations of cell are input into the calibration equation (.alpha., .beta.)=f(xp, yp) to obtain the galvo-mirror angular deflection required to direct the laser (in low power mode) into the correct specimen plane location. At this time, the laser spot can be imaged to determine its actual location in the specimen plane using the detection system. The actual location of the laser relative to the targeted pixel can be used to provide feedback to the guiding algorithm to adjust the laser location, as necessary.

Because of experimental errors and thermal drift, the calibration between pixel location and the laser angular deflection might experience variations that limit the spatial accuracy of the system. Thus, a closed-loop control system that feedbacks the actual location of the laser spot relative to the targeted pixel can be implemented. Once the laser is positioned over the right location, an automatic control can switch the laser to high power mode for a predetermined time duration, inducing the cells to pre-maturely die. During the high power exposure period, the camera chip will be protected by closing a shutter, S1, placed in front of the camera.

To reach the desired depth of ablation, the wavelength of the laser light has to be carefully chosen. For example, a potassium titanyl phosphate laser (KTP) producing light at a 532 nm wavelength is typically used for ablation of tissue limited to surface treatment (for example, skin cancer and tumors at the periphery of organs), as its depth of penetration is only 900 .mu.m. Carbon dioxide lasers are also used for surface ablation as its 10.6 .mu.m wavelength is heavily absorbed by water inside tissue limiting its penetration depth to approximately 300 .mu.m. Alternatively, an ArF excimer laser at around a 248 nm wavelength can be used to treat cells at around 30 .mu.m depth and an XeCl excimer laser at around 308 nm wavelength can be used to treat cells around 50.mu.m depth (Vogel et al., Chem Revv, 103:577-644). A 2.01 .mu.m Cr:Tm:YAG laser has a depth of around 170 .mu.m and a 2.12 .mu.m Cr:Tm:Ho:YAG laser has a depth of around 350 .mu.m (Vogel et al., Chem Revv, 103:577-644). For ablation of diseased tissue below the surface, Nd:YAG lasers, operating at a wavelength of 1064 nm, provide penetration depths up to 15 mm (Reinisch, Otoralyngol. Clin. North. Am., 29:893-914, 1996).

Lasers in the 1-5 W power range are sufficient for ablating tissue with a single nanosecond pulse (Reinisch, Otoralyngol. Clin. North. Am., 29:893-914, 1996). Other powers can be used with accordingly shorter and longer duration treatment periods.

Importantly, quick treatment periods are preferred to ensure that detection and treatment is co-localized and device/patient movement does not affect the treatment accuracy. Several factors affect the speed of the system: (1) image acquisition time (exposure), (2) image processing, (3) ablation time, (4) laser positioning, and (5) number of ablation targets. With 25 million spots (5 cm.times.5 cm of cells) the cumulative laser duration will be about 0.2 seconds if the pulse duration is 1 ns. The speed of the system is mostly limited by a combination of how fast the laser can be moved between targets and how many targets have to be ablated.

Using galvanometer driven mirrors, a laser beam can be scanned over a 500.times.500 pixel in 33 ms (Pawley, Handbook of Biological Confocal Microscopy, 3rd ed) or about 3.3 seconds to ablate 25 million pixels. We expect that in 3.3 seconds, loss of registration would become a problem. To overcome this limitation, we have developed an algorithm to divide the field of view into several small regions to be independently ablated within 0.5 s. Fiducial marks can be generated by the laser to identify each region so the system can automatically detect which regions have been already ablated before moving to the next one. Also, the fiducial marks will allow correct repositioning of the device in case it is moved before ablation has been completed.

Preferably, the pulse duration of the laser and the mirror movement is quick enough to enable image detection and ablation to be co-registered.

A low power laser can also be employed in this invention such that delayed treatment is provided. Specific ablation energy can be delivered to impart nucleic damage to the cell, inducing apoptosis at a future time. DNA absorption is centered around a peak of 260 nm (Vogel et al., Chem Revv, 103:577-644). Alternatively, lasers at other UV and IR wavelengths have been shown to impart DNA damage by various mechanisms (Kong et al., Nucleic Acids Res., 37:e68, Rogakou et al., J. Cell Biol., 146:905-915). Lasers at low enough powers to not induce instantaneous vaporization may be used to impart delayed treatment effects.

Ideally, a laser with appropriate qualities to treat cells at or near the surface of the tissue while sparing deep tissue treatment is preferred in this application. Furthermore, lasers with limited treatment zones are preferred so as not to affect nearby healthy tissue.

To ensure that cell ablation has occurred, a second feedback algorithm can be implemented to detect when the fluorescence of the current target has been extinguished should the treatment energy be sufficient to kill not only the cells, but also the imaging probe as well. After the initial exposure to high power laser is completed, the laser can be switched off, the shutter in front of the camera can be opened and the emission filter can be placed in front of the camera. A second image of the specimen plane can be acquired and compared in a pixel-by-pixel basis with the image acquired pre-ablation. If the current target is still emitting fluorescence, the system can be switched to high power mode for a second exposure. The process can be repeated as necessary. When the current target no longer emits, the nearest fluorescent target can be selected as a new target based on the latest image acquired, and the procedure can be repeated.

With this feedback algorithm, it is important to note that any unactivated imaging agent in healthy tissue may actually be activated with the laser in a "heat affected" zone. A "heat affected" zone would be the tissue which is not completely denatured, but was subjected to above normal temperatures and is located in between that tissue completely ablated and that tissue which was not affected by the laser. Consequently, the laser should be chosen to apply small treatment zones with minimal "heat affected" zones.

Because the tissue exposed during the surgery could have an irregular surface which is not flat, or cancer cells may be one or two layers of cells below the surface, the system can adjust the location of the laser focus to control the depth of ablation. Because the depth of focus of the laser depends on the imaging system properties (numerical aperture, focal length of lenses, diameter of lenses, path length), the optical design can be manipulated to provide an ablation focal depth of approximately 500 .mu.m.

It is possible that the burned tissue or debris generated by laser ablation may interfere with the signal of nearby cells, limiting their detection. The proposed invention also includes an embodiment with a continuous fluid wash which can be applied to the surface to remove any interfering debris. The proposed fluid wash can alternatively be used to cool the tissue such that the focal ablation heats and affects only the desired location while providing minimal impact on healthy tissue.

In other embodiments of the invention, the laser beam is directed to the treatment site by controlling the set of mirrors through the use of a stepper motor or using MEMS mirrors instead of the galvo-mirrors. In a further embodiment, the laser beam can be moved by controlling acousto-optic deflectors. The invention also includes a method of directing the laser beam treatment using micro-mirrors. An acousto-optical modulator used as a deflector, a piezo-electric mirror, an electro-optical deflector, a polygonal mirror, or a planar mirror on a rotating shaft can also be used to direct the laser beam. Any method or combination of methods used to modify the mirror angles such that the laser light energy is directed onto the desired treatment tissue is suitable for this application.

Figure 2:
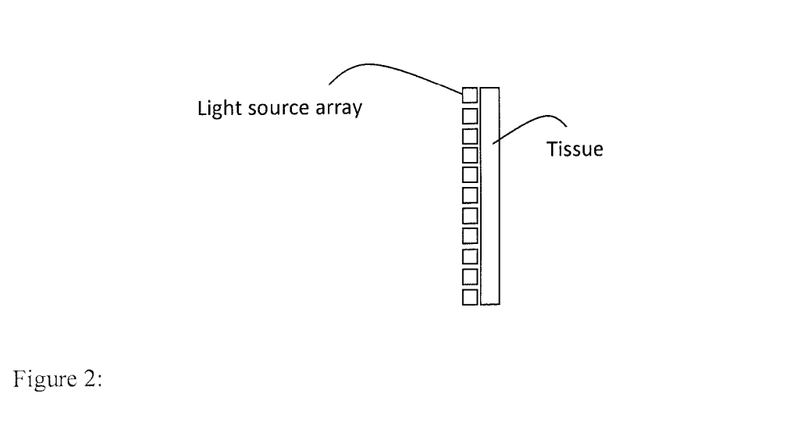
FIG. 2: Light source array used to ablate tissue. Each individual light source is in close enough proximity to the tissue to kill one or more cells.

In other embodiments of this invention, the light source is a single fixed bulb instead of an LED ring. In other embodiments of this invention, the tissue is ablated by using an array of light elements as shown in FIG. 2. Note that the light elements could be light emitting diodes or individual fiber optic bundles or similar sources of energy. In this case each element is preferentially activated in order to selectively ablate the focal tissue closest to the element.

In other embodiments of this invention, the laser is replaced by a radio-frequency (RF) ablation device to similarly impart cellular death. Other embodiments include a cryo-ablation treatment device. Importantly, the micro probes used to deliver the RF energy or cryoablation treatment should be small enough such that a minimal treatment zone is resultant. An array of such micro RF or cryo probes could be controlled easily if applied to the surface of the tissue in place of the light source array pictured in FIG. 2. Each micro probe could be individually controlled creating a targeted treatment area dependent upon the image detection system.

The present invention also includes methods for imaging and treating abnormal cells during an intraoperative surgical procedure. In one aspect, the invention provides a method for spatially determining tissue heterogeneity in a subject undergoing surgery or a minimally invasive intervention by administering a molecular imaging probe to the subject and obtaining an in situ image of the tissue. The image allows for the detection of a diseased cell, if present in the tissue and treatment of detected diseased cells. Furthermore, the method could entail repeating the imaging and treatment steps until no diseased cell is detected in the tissue.

The molecular probe is any molecule that gives us a contrast between the diseased cells and normal tissue and can include either activated, ligand or clearance differential. The activated can be activated by enzymes and can be a flourochrome plus a quencher or two flourochromes in a self-quenching configuration. A ligand based probe would be for instance a flourochrome together with a targeting antibody. A clearance differential probe would be a molecule with a fluorescent label and a pharmacokinetic modifier that clears the probe preferentially from the healthy tissue leaving the cancer cells and/or tumor associated inflammation cells labeled.

In one embodiment, the molecular imaging probe could be administered systemically to the subject or alternatively to the surface of the tissue. Surface administration includes for example spraying or painting. Optionally the molecular imaging probe is administered on a film or sponge. The probe can also be administered orally, parenterally, via bolus injection, or other method used commonly in the surgical practice. Other forms of acceptable administration include subcutaneously, intracutaneously, intravenously, intramuscularly, intraarticularly, intraarterially, intrasynovially, intrasternally, intrathecally, intralesionally, by intracranial injection or infusion techniques, by inhalation spray, rectally, nasally, buccally, vaginally, via an implanted reservoir, by injection, subdermally, intraperitoneally, transmucosally, or in an ophthalmic preparation.

In one embodiment, the molecular imaging probe is an activatable probe. An activatable imaging probe exhibits no fluorescence emission or its fluorescence emission is quenched in its nominal configuration, but its fluorescence emission is typically released upon enzymatic cleavage of its backbone. Activatable imaging probes have been specifically designed to target enzyme families with well established catalytic mechanisms including proteases, kinases, lipases, glycosylases, histone deacylases, and phosphatases. Optimally, the activatable imaging probe targets an enzyme that is either preferentially expressed in cancer cells or is upregulated in cancer cells. Thus, the imaging moiety is only active in cancer cells, allowing for discrimination between cancer and normal tissue. For example, the probe targets an enzyme in the cysteine protease family (e.g., caspase), cysteine cathepsin family (e.g. cathepsin B), serine protease family or the aspartic protease family.

In one embodiment of this invention, the imaging moiety is active in cancer cells as well as tumor-associated cells (eg. tumor-associated macrophages) allowing for discrimination between these cells and normal tissue.

In one embodiment of this invention, the probe is constructed of one or more fluorochromes quenched by each other or quenched through the use of dark quencher molecules, attached together with an enzyme activation site and a pharmacokinetic modifier. Importantly, the pharmacokinetic modifier is adjusted to optimize the administration-to-imaging time spread. After cleavage of the enzyme activation site, the fluorochromes and quenchers are spatially separated allowing fluorescence excitation and detection of the fluorochromes.

A dark quencher emits no fluorescence, but absorbs fluorescence from nearby fluorochromes. Suitable dark quenchers include but are not limited to: QSY (diarylrhodamine derivatives) type quenchers (e.g. QSY21, QSY7, QSY9, QSY35), dabcyl type quenchers, Iowa black FQ and RQ quenchers, and Black Hole quenchers.

The probe fluorochrome is chosen from a group of available compounds in the 350-670 nm visible spectrum to preferentially image cells at or near the tissue surface (within 1 cm) while ignoring deep tissue emission. Suitable examples of fluorochromes in the visible light spectrum which could be used include but are not limited to: Cy3, Cy3.5, Cy5, Alexa 568, Alexa 546, Alexa 610, Alexa 647, ROX, TAMRA, Bodipy 576, Bodipy 581, Bodipy TR, Bodipy 630, VivoTag 645, and Texas Red.

Imaging moieties in the visible light spectrum of 350-670 nm are preferred to selectively view cells at or near the surface (within 1 cm from the surface) and exclude deep tissue emission since the imaged depth of tissue penetration increases as the imaging wavelength increases. Near infrared wavelengths are not needed for this probe application since deep tissue penetration of the energy is not desired. Tissue absorbance and autofluorescence is high between 400 nm and 500 nm while slowly dropping off around 570 nm. Thus the longer wavelengths in the visible spectrum are preferred for this application.

In some embodiments, the molecular imaging probe includes pharmacokinetic modifiers of adjustable molecular weight and size which allows the bio-distribution and diffusion rate of the molecular imaging agent to be controlled. For example, polyethylene glycol (PEG) and/or dextran can be used as a pharmacokinetic modifier because its chain length, and thus molecular weight, can be precisely controlled and readily conjugated to the imaging probe. Other forms of PEG that can be used are polyethylene oxide (PEO) or polyoxyethylene (POE). Other suitable pharmacokinetic modifiers are methoxypolyethylene glycol (MPEG), methoxypolypropylene glycol, polyethylene glycol-diacid, polyethylene glycol monoamine, MPEG monoamine, MPEG hydrazide, MPEG imidazole, copolymers of polyethylene glycol and monoxypolypropylene glycol, branched polypropylene glycol, polypropylene glycol, and polylacic-polyglycolic acid. Optionally, any fatty acid, lipid, phospholipid, carbohydrate, sulfonate, polysulfonate, amino acid, or peptide can be used as a pharmacokinetic modifier to tune the biodistribution of the molecular imaging probe.

Importantly, the size and weight of pharmacokinetic modifiers can be adjusted to modify the kinetics of the probe. Smaller sizes and weights are more useful for surface applications where the probe is directly applied to target tissue and immediate imaging is necessary. Larger sizes and weights allow for the probe to be injected and travel to the target tissue via vascular routes. Further small modifications of the size and weight can be used to adjust the retention time of the probe in the target tissue. In some embodiments the molecular probe needs to reside in the target tissue at least 1 hour and up to 48 hours. Optionally the pharmacokinetic modifiers are optimized to allow imaging within 2 hours of administration or between 12 and 36 hours post probe administration. In some embodiments of the present invention, probes with PEG attachments around 2,000 g/mol and between 20,000 g/mol and 40,000 g/mol are preferably used to target surface applications (small molecular weight PEG) and injectable (larger molecular weight PEG) versions of the molecular imaging probe. Although these are examples, other PEG sizes and different pharmacokinetic modifiers can be used. PEG molecules are typically available in a large array of molecular weights from 300 g/mol to 10,000,000 g/mol.

Preferably, the pharmacokinetic modifier is between 500 g/mol and 100,000 g/mol.

In another embodiment of the present invention, the imaging probe consists of a targeting moiety and an imaging moiety. The imaging moiety can be a fluorochrome and suitable examples of fluorochromes in the visible light spectrum which could be used include but are not limited to: Cy3, Cy3.5, Cy5, Alexa 568, Alexa 546, Alexa 610, Alexa 647, ROX, TAMRA, Bodipy 576, Bodipy 581, Bodipy TR, Bodipy 630, VivoTag 645, and Texas Red.

The targeting moiety preferentially targets diseased tissue and affects the pharmacokinetics in such a way to allow for discrimination between diseased and healthy tissue. In some aspects the targeting moiety binds specifically to CD20, CD33, carcinoembryonic antigen (CEA), alpha fetoprotein (AFP), CA125, CA19-9, prostate specific antigen (PSA), human chorionic gonadotropin (HCG), acid phosphatase, neuron specific enolase, galacatosyl transferase II, immunoglobulin, CD326, her2NEU, EGFR, PSMA, TTF1, Muc, immature glycoslytaion, an EMT marker, a cathepsin, or an enzyme. The targeting moiety can specifically be designed to target enzyme families with well established catalytic mechanisms including proteases, kinases, lipases, glycosylases, histone deacylases, and phosphatases. Once the imaging probe binds to such a target, the probe can be cleared more quickly or less quickly than in normal tissue, allowing for the preferential discrimination between healthy and diseased tissue. Optionally, a pharmacokinetic modifier can be conjugated to the imaging probe to further fine-tune the distribution time properties of the imaging probe. Further, the targeting moiety can be an antibody.

The diseased cell is a tumor cell, or alternatively can be any other abnormal cell or marker of abnormal activity which is fluorescently labeled. For example, one could image tumor-associated macrophages that are typically found surrounding tumors. In another example, one could image abnormal cells in various central nervous system disorders (e.g. Parkinson's disease) or various cardiovascular system disorders (e.g. ischemia), or various orthopedic disorders (e.g. osteoporosis). It should be understood that the above disease areas are not limiting and that other abnormal cells could be detected.

Methods for targeting such tissue could involve conjugating associated molecules to the imaging probe. For example, in various cancer staging, myocardial infarctions, and certain neurological diseases, glucose metabolism is upregulated. Imaging probes further comprising glucose or deoxyglucose molecules could be used to target tissue in need of excess glucose. Furthermore, in malignant tissue, DNA synthesis is upregulated and nucleotide based metabolites such as thymidine are more readily used. Thus, an imaging probe conjugated to thymidine molecules or analogs thereof could be useful in distinguishing cancerous tissue from benign tissue.

In various central nervous system disorders including Parkinson's disease, Tourette's Syndrome, Lesch-Nyhan Syndrom, Rhett's Syndrome, and in substance abuse cases, dopamine metabolism and dopamine transporters are found in increased or decreased prevalence. Imaging these types of diseased cells could involve conjugating the imaging probe to L-dopa, tropanes, dopamine, and/or raclopride molecules which are molecules involved with the dopamine transport into the cytosol of the cell. Importantly, the imaging probe would need to pass the blood brain barrier in this case for a systemic type probe administration.

For the cardiovascular system, the synthesis and breakdown of long chain fatty-acids is indicative of an imbalance of myocardial metabolism commonly found in coronary artery disease, myocardial infarction, cardiomyopathies, or ischemia (Railton et al., 1987 Euro. J NucL. Med. 13:63-67; and Van Eenige et al., 1990 Eur. Hearth 11:258-268). Thus to image these diseased cells, the imaging probe could further be conjugated to one or more long chain fatty acids.

Imbalances in osteoblast activity are involved in osteoporosis, osteoblastic cancer metastases, early calcification in atherosclerotic and cancer lesions, arthritis, and otosclerosis. Since phosphonates and their analogs are found in higher concentrations where osteoblast activity is increased (Zaheer et al., 2001, Nature Biotech 19:1148-1154), then an imaging probe conjugated to phosphonate, phosphonate analogs, methylene diphosphonate, pyrophosphate, and/or alendronate molecules could be useful for imaging such disease states.

Typically tumors and infracted regions are hypoxic. Molecules such as nitroimidizoles and misonidazole accumulate in hypoxic areas and could also be conjugated to an imaging probe to preferentially discriminate hypoxic regions from normal tissue.

Alternatively, the diseased cells are detected without an imaging probe. Instead, the tissue is imaged and then treated. In this case, imaging modalities such as spectroscopy, raman spectroscopy, optical coherent tomography, or auto-fluorescence could be used to detect those cells for further treatment. Furthermore, the imaging system would not need to excite a probe.

Definitions

As used herein, "probe" means an identifiable molecule which is used to detect the presences of other molecules.

As used herein, "fluorochrome" means a molecule which becomes fluorescent by absorbing energy (light) at one or more specific wavelengths by exciting ground-state electrons into a higher energy level and then emitting energy (light) at one or more slightly different wavelengths when the excited electrons return to the ground-state energy level.

As used herein, "dark quencher" means a molecule which absorbs light radiation at one or more specific wavelengths and dissipates the energy absorbed in the form of heat; thus, a dark quencher does not emit fluorescent light.

As used herein, "pharmacokinetic modifier" means a molecule which is attached to the molecular imaging probe which inhibits undesired biodegradation, clearance, or immunogenicity of the probe.

EXAMPLES

Example 1

Interoperative Detection and Ablation of Cancer Tissue

Currently around 50% of breast cancer patients and 35% of sarcoma patients require second tumor de-bulking surgeries because a final pathology report returns days after the initial surgery indicating that residual cancerous cells have been left within the patient. Furthermore, 25% of the final pathology reports do not detect residual cancer cells due to sampling errors fundamentally inherent in the process. Thus, most patients require subsequent medical therapy including additional radiation or chemotherapy treatment to prevent cancer recurrence and metastasis stemming from residual cancer cells. The proposed study aims to investigate an intra-operative method of tumor margin assessment and treatment to ensure negative margins are obtained during the first surgery and additional surgeries are not required.

The intra-operative tumor margin assessment is performed by employing a fluorescence-based imaging system. One day prior to procedure, the patient is injected with an imaging agent activated by enzymes upregulated in cancer tissue. On the day of the surgery, the bulk tumor is manually resected. Then, the tumor bed is examined for residual fluorescence using a wide-field, single cell resolution imaging and ablation device. Locations with high residual fluorescence are determined to consist of residual cancer cells and the ablation feature is activated. Intraoperative diagnosis and treatment is compared to permanent H&E staining of the tissue by a pathologist.

Protocol:

Pre-Operative

Imaging and ablation system is set up in the operating room and is in stand-by mode.

Imaging agent is IV injected into a patient scheduled for bulk tumor resection surgery.

Intra-Operative

The cancer patient undergoes a standard of care tumor resection surgery.

After the gross tumor is removed from the patient, the tumor bed is imaged with the device.

Areas detected with positive fluorescence by the imaging feature are then confirmed by the surgeon and these confirmed areas are ablated.

The tumor bed is cleaned and prepared for a second imaging and ablation sequence.

The tumor bed is re-imaged. Areas which are still fluorescent are displayed to the surgeon. Additional ablation on confirmed areas is performed if so desired by the physician.

Additional tissue samples of areas with positive fluorescence prior to ablation and negative fluorescence post ablation are taken and sent for histological analysis.

A final image of the tumor bed is recorded for future reference.

The wound is closed and the patient recovers from the operation.

Post-Operative

The bulk tumor and any additional tissue samples are assessed by pathology using standard processing techniques.

Positive margins found by pathology are compared to the residual fluorescence images saved during the procedure and additional tissue taken post ablation.

A final determination of the presence of residual cancerous tissue in the tumor bed is made.

Data is recorded to determine if the patient requires an additional surgical procedure due to the presence of residual disease.

Data is recorded to determine the local re-occurrence of disease.

Data is recorded to determine the need for adjuvant care related to the surgical site.

What is claimed is:

1. An in vivo method of treating a subject with a tumor comprising:
   (a) administering a composition comprising a molecular imaging probe to the subject, wherein the imaging probe is a clearance differential probe including a fluorescent label with optical properties in the visible spectrum of 350-670 nm attached to a pharmacokinetic modifier that results in the molecular imaging probe clearing preferentially from healthy tissue leaving tumor cells labeled;
   (b) permitting the molecular imaging probe to clear preferentially from healthy tissue leaving tumor cells labeled;
   (c) performing initial resection surgery to remove cancer cells from the subject thereby creating a resection bed;
   (d) treating the resection bed with light energy and obtaining an in situ image of the bed using an imaging system, wherein the image allows for the detection of the tumor cells, if present in the resection bed; and
   (e) if tumor cells are detected in (d), performing further resection surgery to remove labeled tumor cells.

2. The method of claim 1, wherein the composition is administered systemically to said subject or applied to the surface of said tissue.

3. The method of claim 1 wherein the molecular imaging probe is imaged at between 12 and 36 hours after administration.

4. The method of claim 1, wherein the pharmacokinetic modifier has a molecular weight of between 20,000 g/mol and 40,000 g/mol.

5. The method of claim 1, wherein the pharmacokinetic modifier is selected from the group consisting of polyethylene glycol (PEG), dextran, polyethylene oxide (PEO), polyoxyethylene (POE), methoxypolyethylene glycol (MPEG), methoxypolypropylene glycol, polyethylene glycol-diacid, polyethylene glycol monoamine, MPEG monoamine, MPEG hydrazide, MPEG imidazole, copolymers of polyethylene glycol and monoxypolypropylene glycol, branched polypropylene glycol, polypropylene glycol, and polylacic-polyglycolic acid.

6. The method of claim 1, wherein the molecular imaging probe comprises a polyethylene glycol (PEG) having a molecular weight of between 20,000 g/mol and 40,000 g/mol.

7. The method of claim 1, wherein the fluorescent label is selected from the group consisting of Cy3, Cy3.5, Cy5, Alexa 568, Alexa 546, Alexa 610, Alexa 647, ROX, TAMRA, Bodipy 576, Bodipy 581, Bodipy TR, Bodipy 630, VivoTag 645, and Texas Red.

8. The method of claim 1, wherein the image allows for selective detection of one or more tumor cells within about 1 cm from the surface of the tissue resection bed and excludes deep tissue emission.

9. The method of claim 1, wherein the subject is a human.

10. The method of claim 1, wherein the resolution imaging system comprises: (a) a light source; (b) an optical receptor configured to receive the light from the object; and (c) an image processor.

11. The method of claim 1, wherein the image processor comprises a field of view (FOV) greater than a diameter of a cell of the object and an analysis resolution matched to the diameter of a cell of the object and configured to receive and analyze the light corresponding to each cell in the FOV.

12. The method of claim 1, wherein the imaging probe clears preferentially from healthy tissue leaving both tumor cells and tumor associated inflammation cells labeled.

13. The method of claim 1, wherein the imaging system is a single-cell resolution imaging system.

* * * * *